United States Patent
Bisges et al.

(10) Patent No.: US 8,581,495 B2
(45) Date of Patent: Nov. 12, 2013

(54) APPARATUS FOR PRODUCING PLASMA

(75) Inventors: Michael Bisges, Sinzing (DE); Thorsten Krüger, Regensburg (DE); Patrick Wichmann, Petershagen (DE); Hans-Jürgen Arning, Lübbecke (DE)

(73) Assignee: Reinhausen Plasma GmbH, Regensburg (DE)

( * ) Notice: Subject to any disclaimer, the term of this patent is extended or adjusted under 35 U.S.C. 154(b) by 404 days.

(21) Appl. No.: 13/002,291

(22) PCT Filed: Jun. 30, 2009

(86) PCT No.: PCT/EP2009/058178
§ 371 (c)(1),
(2), (4) Date: Jan. 11, 2011

(87) PCT Pub. No.: WO2010/006920
PCT Pub. Date: Jan. 21, 2010

(65) Prior Publication Data
US 2011/0095688 A1    Apr. 28, 2011

(30) Foreign Application Priority Data
Jul. 2, 2008 (DE) .................. 20 2008 008 731 U

(51) Int. Cl.
*H01J 17/00* (2006.01)
(52) U.S. Cl.
USPC .............................. 315/111.21; 315/111.71
(58) Field of Classification Search
USPC ................ 315/111.21, 111.71; 422/400, 186, 422/186.04
See application file for complete search history.

(56) References Cited

U.S. PATENT DOCUMENTS

| | | | |
|---|---|---|---|
| 6,774,569 B2 * | 8/2004 | de Vries et al. | 315/111.21 |
| 2004/0007985 A1 * | 1/2004 | de Vries et al. | 315/111.91 |
| 2008/0260578 A1 | 10/2008 | Engemann et al. | |
| 2008/0317974 A1 * | 12/2008 | de Vries et al. | 427/569 |
| 2010/0215541 A1 | 8/2010 | Spitzl | |

FOREIGN PATENT DOCUMENTS

| | | |
|---|---|---|
| DE | 197 19 903 | 11/1998 |
| DE | 600 04 975 | 7/2004 |
| DE | 10 2004 049783 | 4/2006 |
| DE | 10 2006 048 815 | 4/2008 |
| DE | 10 2008 045507 | 4/2009 |
| EP | 1790756 | 5/2007 |
| WO | WO 03 059400 | 7/2003 |

OTHER PUBLICATIONS

English Translation of International Preliminary Report on Patentability dated Jan. 27, 2011 issued in corresponding application No. PCT/EP2009/058178.

\* cited by examiner

*Primary Examiner* — David H Vu
(74) *Attorney, Agent, or Firm* — Simpson & Simpson, PLLC

(57) ABSTRACT

An apparatus for producing plasma, includes a container provided with at least one discharge electrode and a power supply unit that has at least one coupling electrode that can be capacitively coupled to the discharge electrode. The power supply unit is adapted to be removable from the container. The at least one coupling electrode is disposed beneath an insulating layer. In this way, the user can not come into direct contact with a coupling electrode after removing the power supply unit.

10 Claims, 3 Drawing Sheets

APPARATUS FOR PRODUCING PLASMA

PRIORITY CLAIM

This is a U.S. national stage of Application No. PCT/EP2009/058178, filed on Jun. 30, 2009, which claims priority to German Application No: 20 2008 008 731.7, filed Jul. 2, 2008 the contents of which are incorporated herein by reference.

BACKGROUND OF THE INVENTION

1. Field of the Invention

The present invention relates to an apparatus for generating plasma with a container, on which at least one discharge electrode is provided and a power supply unit that comprises at least one coupling electrode, which can be capacitively coupled to the discharge electrode.

2. Related Art

DE 10 2004 049 783 shows a device for processing articles arranged in a holding chamber. A wall of dielectric material is provided on the holding chamber; an outside surface of this wall comprises at least two electrodes. A counterelectrode capacitively coupled to the two external electrodes is arranged on an inside surface. By the external electrodes, a voltage can be induced in the internal electrode, which leads to an electrical discharge and to the production of plasma. As a result, the object in the container can be disinfected and sterilized. The coupling electrodes are arranged on the outside surface of the container, so that, in applications that take place in a humid environment, a film of moisture can form on the surface. This film can lead to a short-circuit between the two electrodes. Because the unit is operated at high voltage, the freely accessible electrodes represent a potential hazard to the user. In addition, the electrodes are exposed to environmental influences, so that dirt can cause contacting problems.

SUMMARY OF THE INVENTION

A goal of one embodiment of the present invention is therefore to create an apparatus for generating plasma that guarantees safe operation and is flexible in regard to its applications.

According to one embodiment of the invention, the apparatus comprises a power supply unit that is designed so that it can be removed together with the coupling electrode from the container, wherein the at least one coupling electrode of the power supply unit is arranged under a layer of insulation. As a result, after the power supply unit has been removed, the user cannot come into direct contact with a coupling electrode, which means that safe operation is guaranteed even in a humid environment. The apparatus is therefore also suitable for household use. In addition, the power supply unit can be used with several containers, each of which is provided with a discharge electrode, which can be coupled capacitively to the coupling electrode of the power supply unit. This allows the power supply unit to be used for many containers.

According to a preferred embodiment of the invention, two coupling electrodes are provided, each of which is arranged under an insulating layer. The insulating layer can form a dielectric. As a result, predetermined voltage conditions can be obtained, which allow the continuous production of plasma through discharge.

At least one device is preferably provided for aligning the power supply unit with the container when the unit is placed on it. These devices can be formed by recesses or projections on the container, which cooperate with corresponding features on the power supply unit. As a result of the exact positioning, the distance between the coupling electrodes and the discharge electrode can be adjusted with precision, which improves the operation of the apparatus.

The discharge electrode is preferably arranged on an inside surface of the container. Then, when the voltage is applied through the coupling electrodes, the user cannot come into contact with the discharge electrode, because the discharge electrode is installed so that it is protected from the outside. Alternatively, it is also possible for the discharge electrode to form a section of one of the walls of the container, as a result of which it is readily accessible to the coupling electrodes. Preferably, however, the discharge electrode is at least covered externally by a protective layer.

BRIEF DESCRIPTION OF DRAWINGS

The invention is explained in greater detail below on the basis of several exemplary embodiments, which are illustrated in the attached drawings.

DETAILED DESCRIPTION OF THE DRAWINGS

Figure 1:
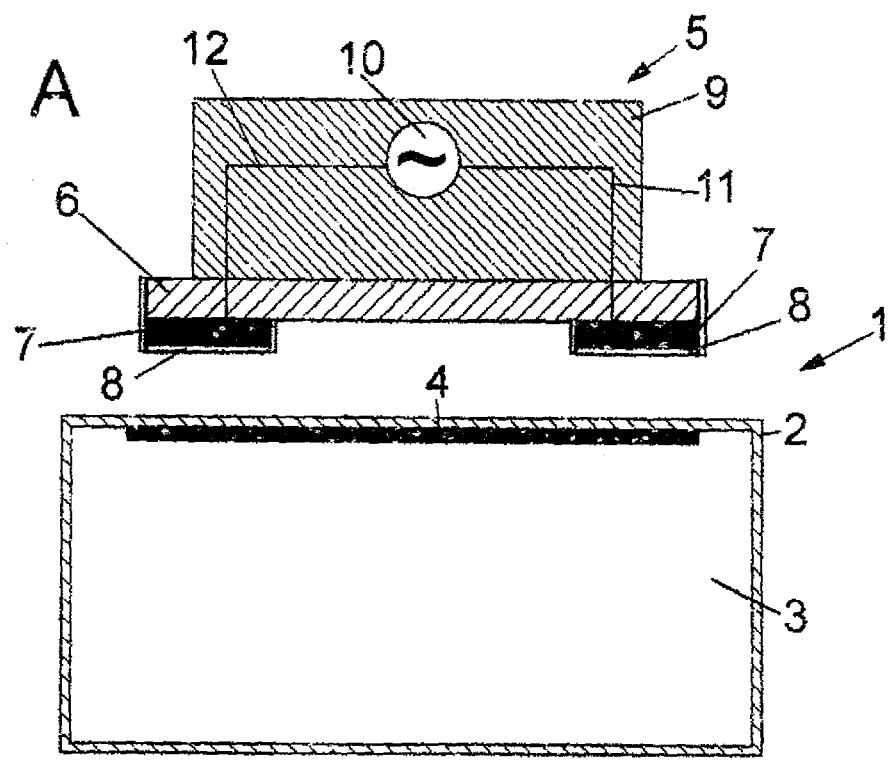
FIGS. 1A and 1B are a first exemplary embodiment of an inventive apparatus for generating plasma.
Figure 1:
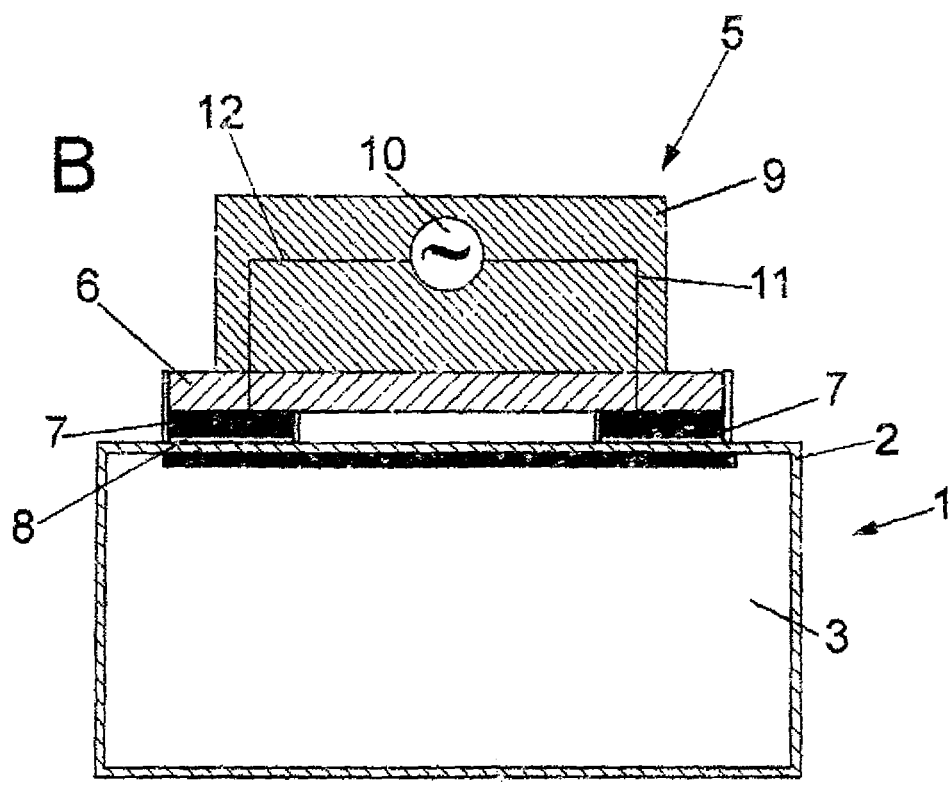

An apparatus 1 for generating plasma comprises a container 2, shown schematically, which can be of a one-piece or multi-part design and which has an interior space 3. A discharge electrode 4, which serves to produce ozone-containing plasma for the treatment of objects in the interior space 3, is arranged on an inside surface of a top wall of the container 2.

The apparatus 1 also comprises a power supply unit 5 that can be removed from the container 2. The power supply unit 5 comprises a support plate 6, on which two coupling electrodes 7 are provided that are arranged under an insulating layer 8. As a result, the coupling electrodes 7 cannot be contacted directly from the outside and do not pose any risk to the user. The coupling electrodes 7 are connected by electrical lines 11 and 12 to a voltage source 10 is installed in a housing 9. The voltage source 10 is shown merely in schematic fashion and can be connected to a power grid, wherein, for operation with low voltage, a transformer, such as a piezoelectric converter can be provided. The power supply unit 5 can be operated at an alternating voltage of 0.5-30 kV at a frequency of 100 Hz to 100 MHz, preferably of 1-30 kHz. As a result of the application of the alternating voltage, the coupling electrodes 7 induce a voltage in the discharge electrode 4, which produces a plasma when it discharges. This ozone-containing plasma can then flow around objects in the container 2 and thus have the effect of sterilizing and disinfecting them.

Figure 2:
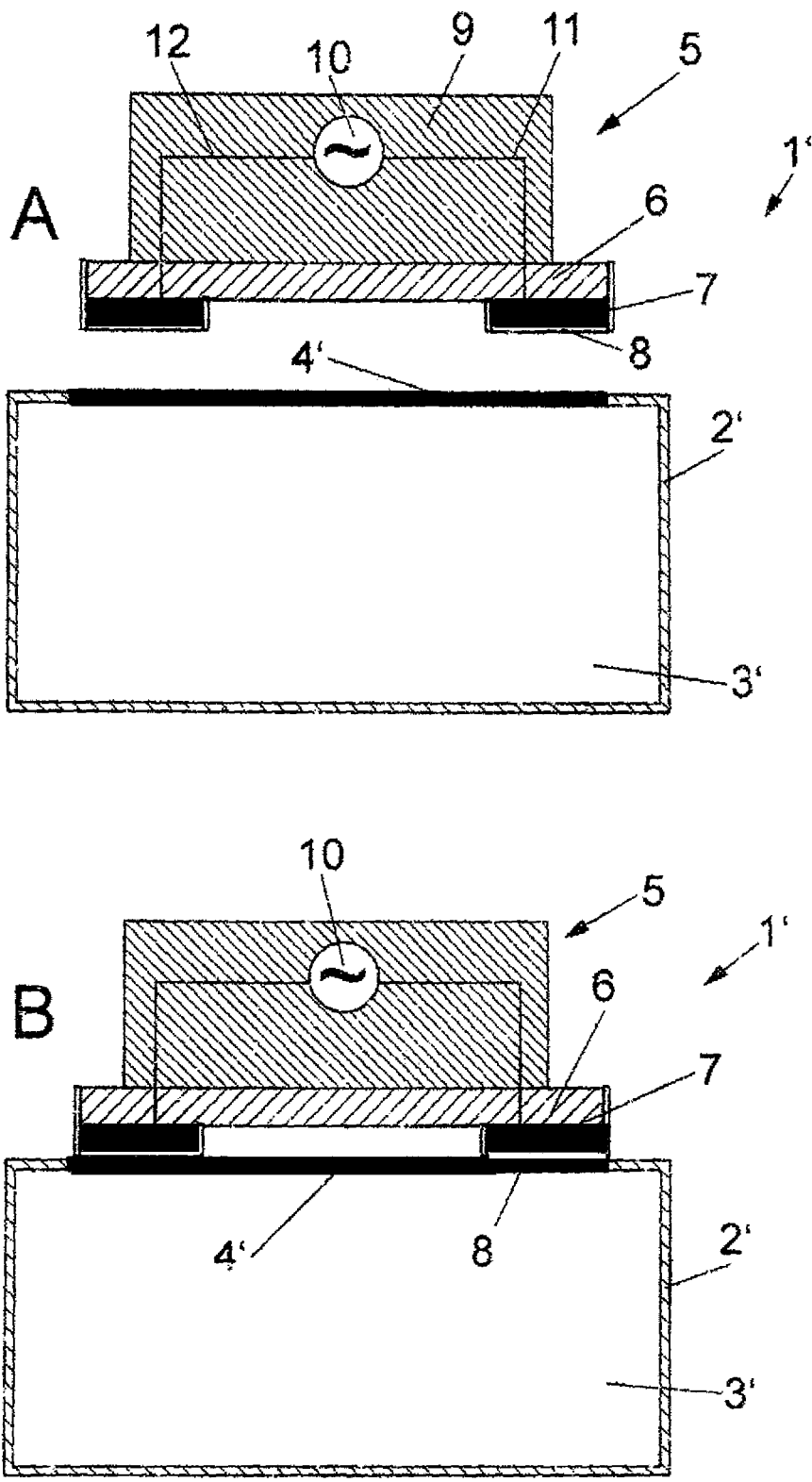
FIGS. 2a and 2B are a second exemplary embodiment of an apparatus for generating plasma.

FIGS. 2A and 2B show a modified embodiment of an apparatus 1' for generating plasma, in which a container 2' comprises a wall section designed to serve as a discharge electrode 4'. This discharge electrode 4' can be arranged, for example, on the cover or a side wall of the container 2'. The power supply unit 5 already known from FIGS. 1A and 1B can be placed on the discharge electrode 4', wherein only the insulating layer 8 over the coupling electrodes 7 acts as a dielectric. As a result, there is only a small amount of insulation between the coupling electrodes 7 and the discharge electrode 4'. The generation of plasma in the interior space 3' of the container 2' has the effect of treating objects in the same way as before.

Figure 3:
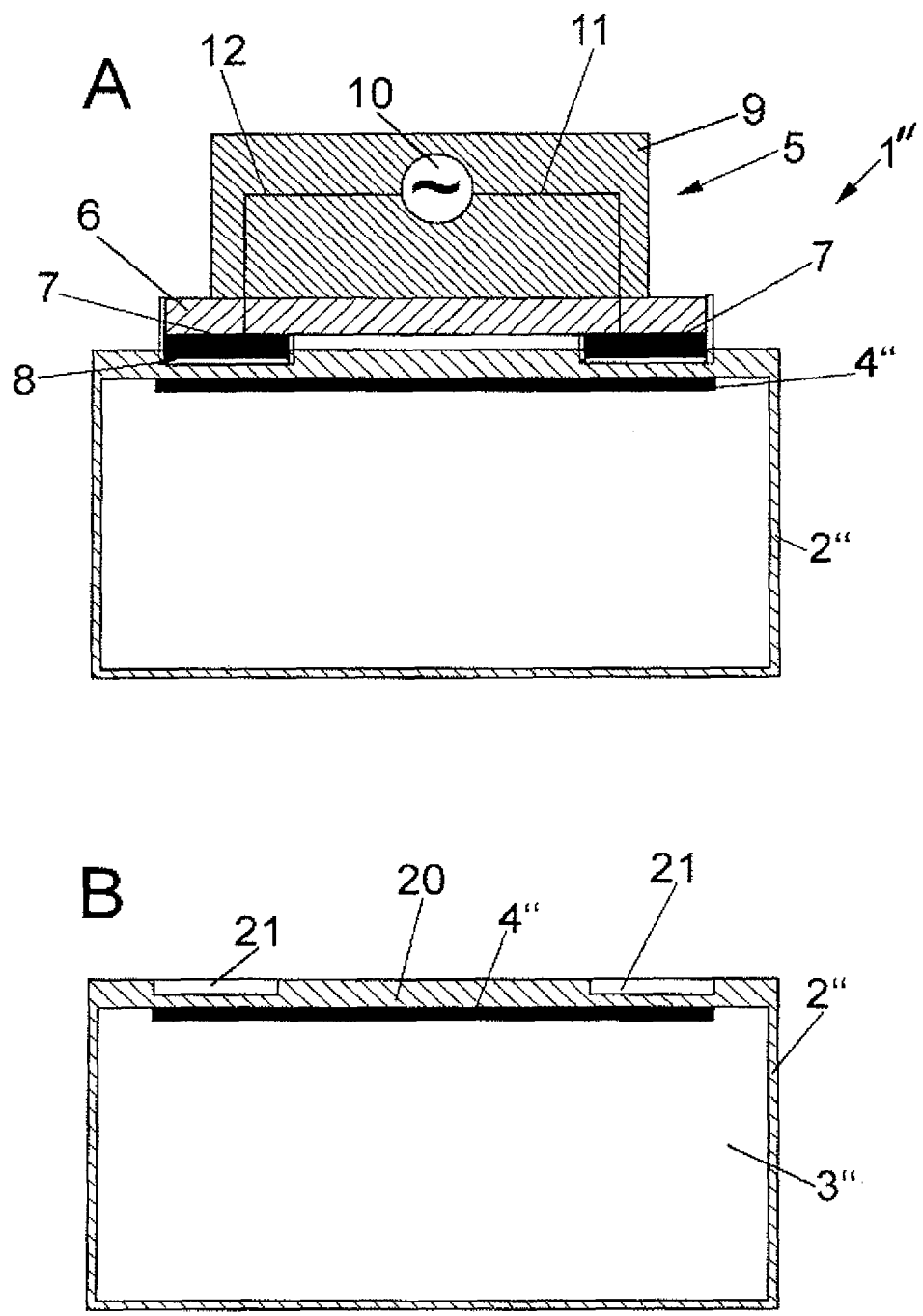
FIGS. 3A and 3B are views of an additional embodiment of an apparatus for generating plasma.

FIGS. 3A and 3B show another embodiment of an apparatus 1" for generating plasma, in which the power supply unit 5 already known from the other exemplary embodiments is used. A container 2" comprises an interior space 3", in which a discharge electrode 4" is provided on an inside wall of the container. In the wall section 20 with the discharge electrode 4", two recesses 21 are provided, into which the coupling electrodes 7' with their insulating layer 8 can be placed in an essentially positive-locking manner. As a result of the recesses 21, the voltage supply unit 5 can be positioned with precision on the container 2", and defined voltage conditions are thus obtained.

In the exemplary embodiments shown here, the power supply unit 5 can be designed with input keys so that it can be programmed. The treatment time, the treatment power level, and the treatment intervals can thus be entered. It is also possible to allow treatment programs to run, during which a certain volume of plasma is produced at predetermined intervals.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An apparatus for generating plasma comprising: a container with at least one discharge electrode provided on the container; and a power supply unit configured to be removeably coupled to the container, comprising: at least one coupling electrode configured to be capacitively coupled to the discharge electrode; and an insulating layer under which the at least one coupling electrode is arranged, wherein the insulating layer prevents contact with the at least one coupling electrode from outside of the apparatus.

2. The apparatus according to claim 1, wherein the power supply unit comprises two coupling electrodes, each of which is arranged under a respective insulating layer.

3. The apparatus according to claim 1, wherein the insulating layer forms a dielectric.

4. The apparatus according to claim 1, further comprising at least one positioning element configured to ensure correct positioning of the power supply unit when it is coupled to the container.

5. The apparatus according to claim 4, wherein at least one of a recess and a projection are arranged on the container and configured to ensure correct positioning of the power supply unit when it is coupled to the container.

6. The apparatus according to claim 1, wherein the discharge electrode is arranged on an inside surface of the container.

7. The apparatus according to claim 1, wherein the discharge electrode forms a section of a wall of the container.

8. The apparatus according to claim 2, further comprising at least one positioning element configured to ensure correct positioning of the power supply unit when it is coupled to the container.

9. The apparatus according to claim 1, wherein at least one of a recess and a projection are arranged on the container and configured to ensure correct positioning of the power supply unit when it is coupled to the container.

10. An apparatus for generating plasma comprising:
 a container including at least one discharge electrode; and
 a power supply unit configured to be removeably coupled to the container and including:
  a support plate;
  an insulating layer; and,
  at least one coupling electrode:
   configured to be capacitively coupled to the discharge electrode; and,
   wholly enclosed by the support plate and the insulating layer such that the at least one coupling electrode cannot be contacted directly from outside the apparatus.

* * * * *